United States Patent [19]

Schönenberger et al.

[11] 4,094,994

[45] June 13, 1978

[54] NOVEL DI-(3'-HYDROXYPHENYL)-ALKANE COMPOUNDS, PROCESS OF PREPARATION AND THEIR USE IN MEDICINE

[75] Inventors: Helmut Schönenberger, Unterhaching; Gerhard Kranzfelder; Helga Schmitt-Wallenborn, both of Munich, all of Germany

[73] Assignee: Klinge Pharma GmbH, Munich, Germany

[21] Appl. No.: 793,321

[22] Filed: May 3, 1977

[30] Foreign Application Priority Data

Dec. 22, 1976 Germany ............................... 2658307

[51] Int. Cl.² ...................... A61K 31/05; A61K 31/09; C07C 39/16; C07C 43/12
[52] U.S. Cl. ............................... 424/341; 260/612 D; 260/613 R; 424/346; 568/729
[58] Field of Search ...................... 260/619 B, 613 R; 424/346, 341

[56] References Cited

U.S. PATENT DOCUMENTS

| 2,382,475 | 8/1945 | Gisvold | 260/619 B |
| 2,400,033 | 5/1946 | Tallman et al. | 260/619 B |
| 3,934,034 | 1/1976 | Manning | 424/346 |

FOREIGN PATENT DOCUMENTS 236,169  6/1945  Switzerland ..................... 260/619 B

*Primary Examiner*—Joseph E. Evans
*Attorney, Agent, or Firm*—Karl W. Flocks

[57] ABSTRACT

Compounds of di-(3'-hydroxyphenyl)-alkanes and their methyl ethers, of the formula

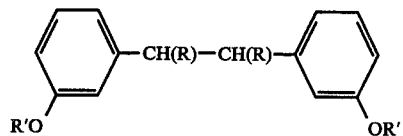

wherein R is alkyl and R' is H or methyl, have activity against hormone-dependent breast carcinoma.

9 Claims, No Drawings

NOVEL DI-(3′-HYDROXYPHENYL)-ALKANE COMPOUNDS, PROCESS OF PREPARATION AND THEIR USE IN MEDICINE

FIELD OF INVENTION

The present invention relates to the treatment of cancer and, more particularly, to new pharmaceuticals particularly useful in inhibiting growth of hormone-dependent breast carcinoma in mammals.

BACKGROUND OF THE INVENTION

It is known that compounds of the stilbene class are capable of inhibiting the growth of hormone-dependent breast tumor cells. However, such compounds, e.g., diethylstilbestrol, generally possess a number of side effects, which are explained in part through their estrogenic properties. While retaining the stilbene nature, it has been possible in some cases to modify the structure to such an extent that, in spite of tumor-inhibiting effect, the estrogenic action was still present in only weakened form. Examples of these compounds that have already found their way into therapy are TAMOXIFEN (i.e., 1-[4′-(2″-dimethylaminoethoxy)-phenyl]trans-1,2-diphenyl-1-butene) and NAFOXIDIN (i.e., 1-[4′-(2″-pyrrolidinethoxy)-phenyl]-2-phenyl-6-methoxy-3,3-dihydro-naphthalene).

Further, it has been determined that, by displacing the hydroxyl groups in diethylstilbestrol from the positions 4,4′ to the positions 3,3′, one obtains a compound which possesses antiestrogenic properties at lower estrogenic activity and thus brings about an inhibition in regard to the growth of hormone-dependent breast tumor cells; see H. Schönenberger et al., Pharmazie 31, 590–597 (1976).

SUMMARY

It has now been unexpectedly found that certain novel compounds from the series of di-(3′-hydroxyphenyl)-alkanes and their methyl ethers turn out as superior in their breast-tumor inhibiting effect on hormone-dependent breast carcinoma of Sprague-Dawley rats (i.e., SD-rat) induced with 7,12-dimethyl-benz[a]-anthracene [i.e., DMBA], as compared with NAFOXIDIN, which is already used in therapy.

DETAILED DESCRIPTION OF EMBODIMENTS

The invention relates to such novel compounds of the general formula (1)

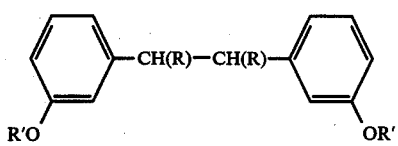

wherein R is a straight or branched alkyl radical comprising 1–6, preferably 1–4 carbon atoms and R′ is a hydrogen atom or a methyl radical. The compounds thus represent an enrichment of the pharmacopoeia and can be used for treating malignant breast tumors. Although the methyl ether compounds provide a desirable effect, the activity is more distinct in the case of the free phenolic compounds.

The invention further relates to a process of preparing compounds of the general formula (1), which is characterized in that compounds of the general formula (2)

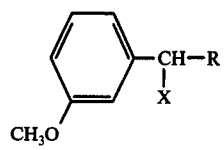

wherein R is a straight or branched alkyl radical comprising 1–6 carbon atoms, preferably 1–4 atoms, and X is a chlorine or bromine atom, are reacted in ether, e.g., diethyl ether, dibutyl ether or even tetrahydrofuran, at temperatures between 0° and 30° C, with 1.5 times molar amount of alkyl magnesium halides of the general formula (3)

wherein R is a lower alkyl radical comprising 1–3 carbon atoms and X is an atom of chlorine, bromine, or iodine, preferably ethyl magnesium bromide, in connection with the addition of 0.075 times molar amount of a waterfree activator, e.g., cobalt - (II) - chloride or nickel - (II) - chloride, preferably cobalt - (II) - chloride (i.e. cobaltous chloride), into compounds of the general formula (4)

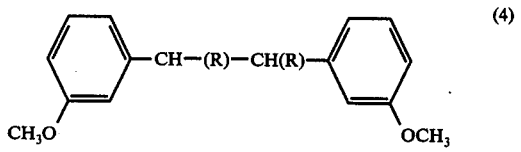

wherein R possesses the significance indicated in the formula (1). In order to prepare the free phenol compounds, the obtained dimerization product is transformed in compounds of the general formula (1), wherein the substituent R′ is a hydrogen atom, by using customary methods of ether splitting (cleavage).

The 1-halogen-1-(3′-methoxyphenyl)-alkanes of the general formula (2) used in the process of the invention can be prepared in various ways. A preferred method consists in reacting 3′-methoxybenzaldehyde in ether, e.g. diethyl ether, diisopropyl ether, dibutyl ether or even tetrahydrofuran, at temperatures between 30° and 100° C, with alkyl magnesium halides of the general formula (5)

wherein R is a straight or branched alkyl radical comprising 1–5, preferably 1–3 carbon atoms, and X is an atom of chlorine, bromine or iodine, into compounds of the general formula (6)

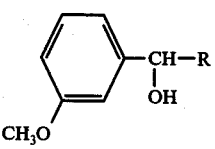

wherein R possesses the significance indicated in the formula (1).

The compounds of the general formula (6) are then transformed into the compounds of the general formula (2), in petroleum ether solution at about 0° C through the introduction of hydrogen chloride or hydrogen bromide, The compounds of the general formula (1) are preferably administered orally. The oral daily dose ordinarily amounts to 0.01–0.3 g, preferably 0.02–0.1 g. Nevertheless, it may be required in a given case to depart from the amounts indicated, namely in dependence on the individual reaction to the medicine or the manner of its formulation and the time or the interval in which the administration takes place. In some cases it may thus be sufficient to use less than the above-mentioned minimal amount, while in other cases one must exceed the above-mentioned upper limit. When larger amounts are used, it is recommended to administer such in several separate doses during the day.

The active substances can be compounded in customary ways for oral administration, e.g., in capsules, tablets, as dragees or even in liquid form, e.g., suspensions or syrups. One or more of the active substances, with or without additional types of active agents, can be worked into tablets or dragee cores by being mixed with solid, pulverulent carrier substances, such as potato starch or cornstarch, additives, such as sodium citrate, calcium carbonate or dicalcium phosphate, and binders such as polyvinyl pyrrolidone, gelatine or cellulose derivatives, possibly by adding also lubricants such as magnesium stearate, sodium lauryl sulfate, "Carbowax" or polyethylene glycols. Of course, taste-improving substances can be added in the case of oral-administration forms.

The therapeutically active compound should be present in a concentration of about 0.5–90% by weight of the total mixture, i.e., in amounts that are sufficient for maintaining the above-mentioned range of dosage.

As further forms of administration, one can use plug capsules, e.g., of hard gelatine, as well as closed soft-gelatine capsules comprising a softener or plasticizer e.g. glycerine. The plug capsules contain the active substance preferably in the form of granulate, e.g., in mixture with fillers, such as lactose, saccharose, mannite, starches, such as potato starch or amylopectin, cellulose derivatives or highly-dispersed silicic acids. In soft-gelatine capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil.

The invention is described more in detail in the following text in reference to specific examples.

The compounds of the invention listed in the following examples are tested by means of thin-layer chromatography in regard to purity (benzene/methanol solvent 9/1, DC-finished plates silica gel 60F$_{254}$, thickness of layer 0.25 mm, firm E. Merck, Darmstadt; detection agent:UV$_{254}$) and secured structurally through $^1$H-NMR-spectroscopy (60 MHz); the chemical shifts are indicated in ppm in relation to tetramethyl silane (TMS, $\delta = 0.0$). the relative intensities are added in brackets. Singlet = s, doublet = d, triplet = t, quartet = q, multiplet = m.

EXAMPLE 1

Preparation of 2,3-di-(3'hydroxyphenyl)-butane (a) 1-(3'-methoxyphenyl)-ethan-1-ol To 166.2 g (1 mol) of methyl magnesium iodide in 150 ml absolute ether, one admixes by drops during stirring a solution of 108.9 g (0.8 mol) 3'-methoxybenzaldehyde in 200 ml ether, and the material is heated for 30 minutes under reflux. Then the mixture is poured onto ice and the precipatate of magnesium hydroxide is dissolved with 5 N HCl. The ether phase is separated, the water phase is extracted with ether a number of times, the combined organic phases are washed with saturated solution of sodium sulfite, then with 10% solution of sodium hydrogencarbonate and finally with water, dried and concentrated in vacuo. Under distillation, the residue produces a colorless oil, boiling point 124° C/11 mm Hg, hRf=61, yield 103,9 g (85.4% of the theory).

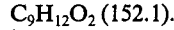

$^1$H - NMR spectrum (CCl$_4$): 1.3 d (3) C$\underline{H}_3$, 3.6 s (3) OC$\underline{H}_3$, 4.7 q (1) C$\underline{H}$, 6.6–7.3 m (4) aromat.

(b) 1-chlor-1-(3'-methoxyphenyl)-ethane

Into a solution of 152.1 g (1 mol) of 1-(3'-methoxyphenyl)-ethan-1-ol in 750 ml petroleum ether, one introduces hydrogen chloride during ice cooling until water separation is completed. The organic phase is then washed with ice-cold water, dried and the petroleum ether is removed in vacuo. The thermo-labile residue is used without any further purification.

Yellow-red oil, hRf = 89, yield 125.0 g (73.3% of the theory).

C$_9$H$_{11}$ClO (170.6).

$^1$H-NMR-spectrum: 1.7 d (3) C$\underline{H}_3$, 3.6 s (3) OC$\underline{H}_3$, 4.9 q (1) C$\underline{H}$, 6.6–7.3 m (4) aromat.

(c) 2,3-di-(3'-methoxyphenyl)-butane

Anhydrous cobaltous chloride in an amount of 6.8 g. (0.052 mol) is introduced during stirring into a solution of 133.2 g (1 mol) ethyl magnesium bromide in 400 ml ether. Into the brown-black solution, there is flowed a solution of 116.0 g (0.68 mol) of 1-chlor-1-(3'-methoxyphenyl)-ethane in 100 ml ether, in portions during stirring at 0° C, in which connection one always waits for the end of gas generation.

The material is then poured onto ice during stirring, the magnesium hydroxide precipitate is dissolved with 5N HCl, the ether phase is separated and the aqueous layer is extracted a number of times with ether. The combined organic phases are washed with water, dried and concentrated in vacuo.

The distillation in vacuo produces an oil (boiling point 140°–150° C/1.5 mm Hg), which crystallizes after left standing for a while or after an addition of methanol; colorless crystals, melting point 96° C (methanol), hRf = 92.

Yield 16.5 g (17.9% of the theory).

C$_{18}$H$_{22}$O$_2$ (270.4) — Calculated: C 79.94, H 8.20; Found: C 80.11, H 7.90.

$^1$H-NMR-spectrum (CDCl$_3$): 1.0 d (6) C$\underline{H}_3$, 2.6–3.0 m (2) C$\underline{H}$. 3.8 s (6) OC$\underline{H}_3$, 6.5–7.4 m (8) aromat.

(d) 2,3-di-(3'-hydroxyphenyl)-butane (α) ether splitting with methyl magnesium iodide To 270.4 g (1 mol) of 2,3-di-(3'-methoxyphenyl)-butane one admixes an etheric solution of 831.0 g (5 mol) methyl magnesium iodide. After ether is evaporated, the material is slowly heated to 170° C during stirring. The cooled-down solid mass is digested with ice water, the precipitate of magnesium hydroxide is dissolved with 5N HCl and the product of reaction is extracted with ether. The ether phase is washed with a saturated solution of sodium thiosulfate and then with water and the 2,3-di-(3'-hydroxyphenyl)-butane is separated from non-decomposed methyl ester through extraction with 0.5 N sodium hydroxide. The alkaline solution is then acidified with 5 N HCl, extracted with ether, the ether layer is washed, dried and concentrated in vacuo. The residue is recrystallized from glacial acetic acid/water for the purpose of further purification.

($\beta$) Ether splitting with pyridine hydrochloride 270.4 g (1 mol) of 2,3-di-(3'-methoxyphenyl)-butane and 693.4 g (6 mol) anhydrous pyridine hydrochloride are slowly heated to 220° C during stirring. The melt is poured into ice water, the precipitate is dissolved in ether and the final product is isolated in accordance with the process of $\alpha$).

Colorless crystals, melting point 163° C (glacial acetic acid/water), hRf = 28.

Yield: process ($\alpha$): 186.6 g (77.0% of the theory), process ($\alpha$): 222.9 g (92.0% of the theory).

$C_{16}H_{18}O_2$ (242.3) — Calculated: C 79.30, H 7.48; Found: C 79.73, H 7.43.

$^1$H-NMR-spectrum (CD$_3$OD): 1.0 d (6) C$\underline{H}_3$, 2.7 q (2) C$\underline{H}$, 6.5–7.3 m (8) aromat.

EXAMPLE 2

Preparation of 3,4-di-(3'-hydroxyphenyl)-hexane (a) 1-(3'-methoxyphenyl)-propan-1-ol The preparation was effected in analogy to example 1(a) from 3'-methoxybenzaldehyde and ethyl magnesium bromide.

Colorless oil, boiling point = 134° C/10 mm Hg, hRf = 65.

Yield 70.2% of the theory.
$C_{10}H_{14}O_2$ (166.2).
$^1$H-NMR-spectrum: 0.8 t (3) C$\underline{H}_3$, 1.7 m (2) C$\underline{H}_2$, 3.6 s (3) OC$\underline{H}_3$, 4.4 t (1) C$\underline{H}$, 6.6 – 7.4 (4) aromat.

(b) 1-chlor-1-(3'-methoxyphenyl)-propane

The preparation was effected in analogy to example 1(b) from 1-(3'-methoxyphenyl)-propan-1-ol and HCl gas.

Colorless oil, boiling point = 87° C/0.4 mm Hg, hRf = 89.

Yield 93.2% of the theory.
$C_{10}H_{13}ClO$ (184.5).
$^1$H-NMR-spectrum: 0.9 t (3) C$\underline{H}_3$, 2.0 m (2) C$\underline{H}_2$, 3.6 s (3) OC$\underline{H}_3$, 4.7 t (1) C$\underline{H}$, 6.6 – 7.3 m (4) aromat.

(c) 3,4-di-(3'-methoxyphenyl)-hexane

The preparation was effected in analogy to example 1(c) from 1-chlor-1-(3'-methoxyphenyl)-propane and ethyl magnesium bromide activated with cobalt-(II)-chloride.

Colorless crystals, melting point 88° C (methanol), hRf=91, boiling point = 145°–155° C/1 mm Hg.

Yield 25.0% of the theory.

$C_{20}H_{26}O_2$ (298.4) — Calculated: C 80.50, H 8.72; Found: C 80.69, H 8.43.

$^1$H-NMR-spectrum (CCl$_4$): 0.6 t (6) C$\underline{H}_3$, 1.1–1.7 m (4) C$\underline{H}_2$, 2.3–2.7 m (2) C$\underline{H}$, 3.8 s (3) OC$\underline{H}_3$, 6.5–7.4 m (8) aromat.

(d) 3,4-di-(3'-hydroxyphenyl)-hexane

The preparation was effected in analogy to example 1(d) from 3,4-di-(3'-methoxyphenyl)-hexane.

Colorless crystals, melting point 174° C (benzene/ether), hRf = 28.

Yield 83.0% of the theory (process $\alpha$), 91.0% of the theory (process $\beta$).

$C_{18}H_{22}O_2$ (270.4) — Calculated: C 79.94, H 8.20; Found: C 80.16, H, 7.92.

$^1$H-NMR-spectrum (CD$_3$OD): 0.5 t (6) C$\underline{H}_3$, 1.0–1.7 m (4) C$\underline{H}_2$, 2.3–2.6 m (2) C$\underline{H}$, 6.5–7.3 m, (8) aromat.

EXAMPLE 3

Preparation of 4,5-di-(3'-hydroxyphenyl)-octane (a) 1-(3'-methoxyphenyl)butan-1-ol The preparation was effected in analogy to example 1(a) from 3'-methoxybenzaldehyde and propyl magnesium bromide.

Yellowish oil, boiling point = 136° C/10 mm Hg: hRf = 69.

Yield 84.3% of the theory.
$C_{11}H_{16}O_2$ (180.2).
$^1$H-NMR-spectrum (CCl$_4$): 0.6–1.8 m (7) C$\underline{H}_2$C$\underline{H}_2$C$\underline{H}_3$, 3.7 s (3) OC$\underline{H}_3$, 4.4 t (1) C$\underline{H}$, 6.6–7.3 m (4) aromat.

(b) 1-chlor-1-(3'-methoxyphenyl)-butane

The preparation was effected in analogy to example 1(b) from 1-(3'-methoxyphenyl)-butan-1-ol and HCl-gas.

Yellow oil, hRf = 89.
Yield 93.0% of the theory.
$C_{11}H_{15}ClO$ (198.7).
$^1$H-NMR-spectrum: 0.7–2.3 m (7) C$\underline{H}_2$C$\underline{H}_2$C$\underline{H}_3$, 3.6 s (3) OC$\underline{H}_3$, 4.8 t (1) C$\underline{H}$, 6.6–7.4 m (4) aromat.

(c) 4,5-di-(3'-methoxyphenyl)-octane

The preparation was effected in analogy to example 1(c) from 1-chlor-1-(3'-methoxyphenyl)-butane and ethyl magnesium bromide activated with cobalt - (II) - chloride.

Colorless crystals, melting point 80° C (methanol), hRf=91.

Boiling point = 158°–162° C/1.5 mm Hg.
Yield 11.0% of the theory.
$C_{22}H_{30}O_2$ (326.5) — Calculated: C 80.94, H 9.26; Found: C 80.86, H 9.04.

$^1$H-NMR-spectrum (CCl$_4$): 0.5–1.7 m (14) C$\underline{H}_2$C$\underline{H}_2$C$\underline{H}_3$, 2.4–2.8 m (2) C$\underline{H}$, 3.8 s (6) OC$\underline{H}_3$, 6.5–7.3 m (8) aromat.

(d) 4,5-di-(3'-hydroxyphenyl)-octane

The preparation was effected in analogy to example 1(d) from 4,5-di-(3'-methoxyphenyl)-octane.

Colorless crystals, melting point 161° C (glacial acetic acid/water).

hRf = 33.
Yield 72.0% of the theory (process $\alpha$), 89.0% of the theory (process $\beta$).

$C_{20}H_{26}O_2$ (298.4) — Calculated: C 80.49, H 8.78; Found: C 80.55, H 8.52.

$^1$H-NMR-spectrum (CD$_3$OD): 0.5–1.6 m (14) C$\underline{H}_2$C$\underline{H}_2$C$\underline{H}_3$, 2.5–2.7 m (2) C$\underline{H}$, 6.5–7.3 m (8) aromat.

EXAMPLE 4

Preparation of 2,5-dimethyl-3,4-di-(3'-hydroxyphenyl)-hexane (a) 1-(3'-methoxyphenyl)-2-methylpropan-1-ol The preparation was effected in analogy to example 1(a) from 3'-methoxybenzaldehyde and isopropyl magnesium bromide.

Colorless oil, boiling point 113° C/0.7 mm Hg, hRf = 67.

Yield 78.5% of the theory.

$C_{11}H_{16}O_2$ (180.2).

$^1$H-NMR-spectrum (CCl$_4$): 0.8 d (3) C$\underline{H}_3$, 0.9 d (3) C$\underline{H}_3$, 1.5–2.2 m (1) C$\underline{H}$(CH$_3$)$_2$, 3.8 s, (3) OC$\underline{H}_3$, 4.2 d (1) C$\underline{H}$OH, 6.6–7.3 m (4) aromat.

(b) 1-chlor-1-(3'-methoxyphenyl)-2-methyl-propane

The preparation was effected in analogy to example 1(b) from 1-(3'-methoxyphenyl)-2-methyl-propan-1-ol and HCl-gas.

Red oil, hRf = 89.

Yield 98.0% of the theory.

$C_{11}H_{15}ClO$ (198.7).

$^1$H-NMR-spectrum (CCl$_4$): 0.8 d (3) C$\underline{H}_3$, 1.1 d (3) C$\underline{H}_3$, 1.7–2.5 m (1) C$\underline{H}$(CH$_3$)$_2$, 3.7 s (3) OC$\underline{H}_3$, 4.6 d (1) C$\underline{H}$Cl, 6.6–7.4 m (4) aromat.

(c) 2,5-dimethyl-3,4-di-(3'-methoxyphenyl)-hexane

The preparation was effected in analogy to example 1(c) from 1-chlor-1-(3'-methoxyphenyl)-2-methyl-propane and ethyl magnesium bromide activated with cobalt - (II) - chloride.

Colorless crystals, melting point 169° C (methanol), hRf = 91, boiling point = 155°–165° C/1.5 mm Hg.

Yield 10.0% of the theory.

$C_{22}H_{30}O_2$ (326.5) — Calculated: C 80.94, H 9.26; Found: C 80.84, H 9.12.

$^1$H-NMR-spectrum (CCl$_4$): 0.6 d (6) C$\underline{H}_3$, 0.7 d (6) C$\underline{H}_3$, 1.4–2.1 m (2) C$\underline{H}$(CH$_3$)$_2$, 3.0 m (2) C$\underline{H}$, 3.8 s (6) OC$\underline{H}_3$, 6.5–7.4 m, (8) aromat.

(d) 2,5-dimethyl-3,4-di-(3'-hydroxyphenyl)-hexane

The preparation was effected in analogy to example 1(d) from 2,5-dimethyl-3,4-di-(3'-methoxyphenyl)-hexane.

Colorless crystals, melting point 232° C (glacial acetic acid/water), hRf=33.

Yield 68.0% of the theory (process α), 90.0% of the theory (process β).

$C_{20}H_{26}O_2$ (298.4) — Calculated: C 80.49, H 8.78; Found: C 80.17, H 8.31.

$^1$H-NMR-spectrum (d$_6$-DMSO): 0.5 d (6) C$\underline{H}_3$, 0.6 d (6) C$\underline{H}_3$, 1.3–2.0, m (2) C$\underline{H}$(CH$_3$)$_2$, 3.0 m (2) C$\underline{H}$, 6.5–7.3 m (8) aromat.

EXAMPLE 5

Preparation of 5,6-di-(3'-hydroxyphenyl)-decane (a) 1-(3'-methoxyphenyl)-pentan-1-ol The preparation was effected in analogy to example 1(a) from 3'-methoxybenzaldehyde and butyl magnesium bromide.

Yellowish oil, boiling point 180° C/0.2 mm Hg, hRf=72.

Yield 79.0% of the theory.

$C_{12}H_{18}O_2$ (194.2).

$^1$H-NMR-spectrum (CCl$_4$): 0.6–1.8 m (9) (C$\underline{H}_2$)$_3$CH$_3$, 3.7 s (3) OC$\underline{H}_3$, 4.4 t (1) C$\underline{H}$, 6.6–7.3 m (4) aromat.

(b) 1-chlor-1-(3'-methoxyphenyl)-pentane

The preparation was effected in analogy to example 1(b) from 1-(3'-methoxyphenyl)-pentan-1-ol and HCl-gas.

Yellowish oil, hRf=89.

Yield 64.0% of the theory.

$C_{12}H_{17}ClO$ (212.7).

$^1$H-NMR-spectrum (CCl$_4$): 0.6–2.3 m (9) (C$\underline{H}_2$)$_3$C$\underline{H}_3$, 3.7 s (3) OC$\underline{H}_3$, 4.7 t (1) C$\underline{H}$, 6.6–7.3 m (4) aromat.

(c) 5,6-di-(3'-methoxyphenyl)-decane

The preparation was effected in analogy to example 1(c) from 1-chlor-1-(3'-methoxyphenyl)-pentane and ethyl magnesium bromide activated with cobalt - (II) - chloride.

Yellowish oil, boiling point 175° C/0.2 mm Hg, hRf=91.

Yield 13.0% of the theory.

$C_{24}H_{34}O_2$ (354.5) — Calculated: C 81.34, H 9.66; Found: C 81.36, H 9.71.

$^1$H-NMR-spectrum (CCl$_4$): 0.5–2.2 m (18) (C$\underline{H}_2$)$_3$CH$_3$, 2.3–2.8 m (2) C$\underline{H}$, 3.7 s (6) OC$\underline{H}_3$, 6.2–7.4 m (8) aromat.

(d) 5,6-di-(3'-hydroxyphenyl)-decane

The preparation was effected in analogy to example 1(d) from 5,6-di-(3'-methoxyphenyl)-decane.

Colorless crystals, melting point 158° C (glacial acetic acid/water), hRf=36.

Yield 59.0% of the theory (process α), 85.0% of the theory (process β).

$C_{22}H_{30}O_2$ (326.5) — Calulated: C 80.93, H 9.26; Found: C 81.25, H 8.91.

$^1$H-NMR-spectrum (CD$_3$OD): 0.5–1.6 m (18) (C$\underline{H}_2$)$_3$CH$_3$, 2.4–2.7 m (2) C$\underline{H}$, 6.5–7.3 m (8) aromat.

EXAMPLE 6

Preparation of 6,7-di-(3'-hydroxyphenyl)-dodecane (a) 1-(3'-methoxyphenyl)-hexan-1-ol The preparation was effected in analogy to example 1(a) from 3'-methoxybenzaldehyde and pentyl magnesium bromide.

Yellowish oil, boiling point 110° C/0.2 mm Hg, hRf=75

Yield 90.1% of the theory.

$C_{13}H_{20}O_2$ (208.2).

$^1$H-NMR-spectrum (CCL$_4$): 0.6–1.9 m (11) (C$\underline{H}_2$)$_4$C$\underline{H}_3$, 3.7 s (3) OC$\underline{H}_3$, 4.4 t (1) C$\underline{H}$, 6.6–7.3 m (4) aromat.

(b) 1-chlor-1-(3'-methoxyphenyl)-hexane

The preparation was effected in analogy to example 1(b) from 1-(3'-methoxyphenyl)-hexan-1-ol and HCl-gas.

Yellowish oil, hRf=89.

Yield 98.0% of the theory.

$C_{13}H_{19}ClO$ (226.7).

$^1$H-NMR-spectrum (CCl$_4$): 0.6–2.3 m (11) (C$\underline{H}_2$)$_4$C$\underline{H}_3$, 3.7 s (3) OC$\underline{H}_3$, 4.7 t (1) C$\underline{H}$, 6.6–7.3 m (4) aromat.

(c) 6,7-di-(3'-methoxyphenyl)-dodecane

The preparation was effected in analogy to example 1(c) from 1-chlor-1-(3'-methoxyphenyl)-hexane and ethyl magnesium bromide activated with cobalt - (II) - chloride.

Yellowish oil, boiling point 145°–170° C/0.1 mm Hg, hRf-91

Yield 37.0% of the theory.

$C_{26}H_{38}O_2$ (382.6) — Calculated: C 81.62, H 10.01; Found: C 81.73, H 10.06.

$^1$H-NMR-spectrum (CDCl$_3$): 0.5–2.2 mm (22) (CH$_2$)$_4$CH$_3$, 2.4–3.0 m (2) CH, 3.7 s (3) OCH$_3$, 3.8 s (3) OCH$_3$, 6.3–7.4 m (8) aromat.

(d) 6,7-di-(3'-hydroxyphenyl)-dodecane

The preparation was effected in analogy to example 1(d) from 6,7-di-(3'-methoxyphenyl)-dodecane.

Colorless crystals, melting point 156° C (Glacial acetic acid/water), hRf=39.

Yield 53.0% of the theory (process α), 92.0% of the theory (process β).

$C_{24}H_{34}O_2$ (354.5) — Calculated: C 81.30, H 9.66; Found: C 81.03, H 9.38.

$^1$H-NMR-spectrum (CD$_3$OD): 0.5–1.8 m (22) (CH$_2$)$_4$CH$_3$, 2.6 m (2) CH, 6.5–7.4 m (8) aromat.

EXAMPLE 7

Medicine containing 3,4-di-(3'-hydroxyphenyl)-hexane

Twenty g of pulverized 3,4-di-(3'-hydroxyphenyl)-hexane is mixed with 20 g lactose and 70 g starch, then with 16.5 g talcum and 6.5 g calcium stearate. After the material is thoroughly mixed, it is filled into 1000 hard gelatine capsules of suitable size, so that each capsule contains 20 mg active substance.

EXAMPLE 8

Medicine containing 2,3-di-(3'-hydroxyphenyl)-butane

Twenty g of 2,3-di-(3'-hydroxyphenyl)-butane are dissolved in 480 g olive oil and filled into 2000 capsules, content 250 mg, in accordance with the Scherer process, so that each capsule contains 10 mg active substance.

EXAMPLE 9

Pharmacological testing (a) Tumor-inhibiting effect

The tumor-inhibiting effect was tested on groups of 8–12 normally fed (Altromin R-standard feed) female Sprague-Dawley rats, weight 200–250 g, possessing a hormone-dependent breast carcinoma induced by 7,12-dimethylbenz[a]anthracene[2].

[2] E. Hoffman, Dissertation, University of Munich, 1974.

The test compounds were dissolved in olive oil at 0.2% and administered subcutaneously through a period of 21 days three times per week (Monday, Wednesday, Friday) in an amount of 2 mg/kg body weight.

At the start of the experiment and on the 21st day of the experiment, the tumor surfaces of the animals subjected to the therapy (=T) and of control animals (=C) were measured and the quotient of the surfaces (=T/C) was determined. The index T/C is valid as expression of the tumor-inhibiting activity of the compounds (see table 1).

Table 1

| Tumor-inhibiting activity of the test substances | |
|---|---|
| Compound | T/C |
| Comparison substances | |
| a) NAFOXIDIN | 0.65 |
| b) diethylstilbestrol | 0.37 |
| Test substances | |
| 2,3-di-(3'-hydroxyphenyl)-butane | 0.49 |
| 3,4-di-(3'-hydroxyphenyl)-hexane | 0.08 |

Table 1-continued

| Tumor-inhibiting activity of the test substances | |
|---|---|
| Compound | T/C |
| 4,5-di-(3'-hydroxyphenyl)-octane | 0.32 |

(b) Estrogenic effect

The estrogenic effect was determined in the uterus-weight test on the mouse in accordance with the method of R. I. Dorfman.[3]

[3] R. I. Dorfman, Methods in Hormone Research II, page 707, Academic Press, New York, London, 1962.

Table 2

| Uterotrophic activity of the test substances | | |
|---|---|---|
| Compound | Dose[x] (μg/mouse/d) | Uterotrophic effect[xx] |
| Comparison substances | | |
| a) NAFOXIDIN | 1 μg | 56% |
| b) diethylstilbestrol | 0.21 μg | 100% |
| Test compounds | | |
| 2,3-di-(3'-hydroxyphenyl)-butane | 650 μg | 4% |
| 3,4-di-(3'-hydroxyphenyl)-hexane | 80 μg | 66% |
| 4,5-di-(3'-hydroxyphenyl)-octane | 900 μg | 84% |

[x]Dose for obtaining the maximally attainable uterus weight in μg
[xx]Maximally attainable increase in uterus weight in percent
Estrone standard: 0.21 μg/mouse/d = 100%

(c) Antiestrogenic activity

The antiestrongenic activity was determined in the uterus-weight test on the mouse in accordance with the method of R. I. Dorfman.[3]

Table 3

| Antiuterotrophic activity of the test substances | | | |
|---|---|---|---|
| Compound | Dose[x] (μg/mouse/d) | Antiuterotrophic effect[xx] | Uterotrophic effect[xxx] |
| Comparison substance | | | |
| NAFOXIDIN | 30 μg | 45% | 50% |
| Test compounds | | | |
| 2,3-di-(3'-hydroxyphenyl)-butane | 500 μg | 32% | 0% |
| 3,4-di-(3'-hydroxyphenyl)-hexane | 5 μg | 53% | 10% |
| 4,5-di-(3'-hydroxyphenyl)-octane | 50 μg | 43% | 34% |

[x]Dose for obtaining the maximally attainable inhibition of the estrone-induced increase in the weight of uterus in μg
[xx]Maximally attainable inhibition of the estrone (0.1 μg/mouse/d)-induced increase in the weight of uterus, in percent
[xxx]Increase in the weight of uterus in percent subsequently to the application of the inhibitor dose, which produces a maximal antiuterotrophic effect.
Estrone standard : 0.21 μg/mouse/d = 100%

It is to be understood that the invention is not limited to the embodiments disclosed above which are illustratively offered, and that modifications may be made without departing from the scope of the invention.

What is claimed is:

1. A di-(3'-hydroxyphenyl)-alkane compound of the general formula (1)

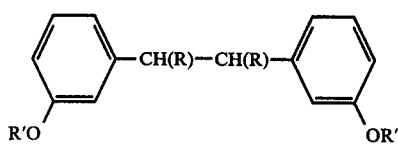

wherein R is a straight or branched alkyl of 1–6 carbon atoms and R' is hydrogen or methyl.

2. 3,4-di(3'-hydroxyphenyl)-hexane, in accordance with claim 1.

3. 2,3-di(3'-hydroxyphenyl)-butane, in accordance with claim 1.

4. 4,5-di-(3'-hydroxyphenyl)-octane, in accordance with claim 1.

5. A process of preparing the compound of claim 1, comprising reacting a compound of the formula (2)

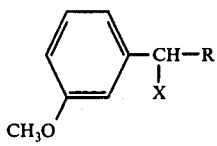 (2)

wherein R is a straight or branched alkyl of 1-6 carbon atoms and X is chlorine or bromine, with an alkyl magnesium halide of the general formula (3)

R — Mg — X (3)  (3)

wherein R is a lower alkyl of 1-3 carbon atoms and X is chlorine, bromine or iodine, in the presence of water-free cobaltous - (II) - or nickelous - (II) - chloride.

6. A process in accordance with claim 5 wherein the obtained dimerization product is then subjected to ether splitting.

7. A pharmaceutical composition for treatment of breast carcinoma comprising a compound in accordance with claim 1 in a breast-carcinoma-growth-inhibiting quantity and a pharmaceutical carrier.

8. A composition as in claim 7, in single dose form and comprising 10-300 mg of said compound.

9. A method for treating breast carcinoma in a mammal comprising orally, parenterally, or subcutaneously administering to said mammal a breast-carcinoma-growth-inhibiting amount of the compound of claim 1.

* * * * *